US00PP09408P

United States Patent [19]

Rother

[11] Patent Number: Plant 9,408

[45] Date of Patent: Dec. 26, 1995

[54] PETUNIA PLANT NAMED 'PAMPAS FIRE'

[76] Inventor: Reinhard W. Rother, 56 Monhulk Emerald Road, Emerald, Victoria 3782, Australia

[21] Appl. No.: 193,434

[22] Filed: Feb. 8, 1994

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

| | | | |
|---|---|---|---|
| P.P. 6,722 | 4/1989 | De Jong | Plt./68.1 |
| P.P. 6,899 | 7/1989 | Tsuda et al. | Plt./68.1 |
| P.P. 6,914 | 7/1989 | Tsuda et al. | Plt./68.1 |
| P.P. 6,915 | 7/1989 | Tsuda et al. | Plt./68.1 |
| P.P. 7,150 | 2/1990 | Vletter | Plt./68.1 |
| P.P. 7,224 | 5/1990 | Rosendal | Plt./68.1 |
| P.P. 7,270 | 7/1990 | Schwyn | Plt./68.1 |
| P.P. 7,344 | 10/1990 | Bloom et al. | Plt./68.1 |
| P.P. 7,400 | 12/1990 | Tvrtkovic-Sahin et al. | Plt./68.1 |
| P.P. 7,544 | 6/1991 | Lamont | Plt./68.1 |
| P.P. 8,015 | 10/1992 | Falstad, III | Plt./68.1 |
| P.P. 8,158 | 2/1993 | Dehan | Plt./68.1 |
| P.P. 8,352 | 8/1993 | Zemach | Plt./68.1 |
| P.P. 8,388 | 9/1993 | Akerboom | Plt./68.1 |

OTHER PUBLICATIONS

Heiser et al., Nightshades The Paradoxical Plants, W. H. Freeman and Co. Publsiher (1969).

Milne, Lorus and Margery, Living Plants of the World, Random House, N.Y. Publisher (1975).

Simpson and Conner–Ogorzaly, Economic Botany—Plants in Our World, McGraw–Hill Book Co. Publisher (1986).

*Primary Examiner*—James R. Feyrer

*Attorney, Agent, or Firm*—Brown, Martin, Haller & McClain

[57] ABSTRACT

A new and distinct variety of *Petunia axillaris* plant called "Pampas Fire" is described. The variety is a prostate, diffuse spreading, viscid glandular pubescent perennial with spreading or handing leaves and reaching a length of 1 meter or more. The leaves are ovate and about 3–4 cm long×1–2 cm wide; early leaves are commonly larger than later leaves, and some early leaves are exceptionally large. The savlerform, pendulous flowers have a red purple corolla, purple violet backs of the petals and tube, and blue veins of petals and tube. The variety is tolerant of a wide range of temperatures, especially higher temperatures, has a high growth rate and is ever blooming with a high concentration of blooms.

1 Drawing Sheet

BACKGROUND OF THE VARIETY

The present invention related to a new and distinct variety of petunia plant which is obtained by clonal selection from a number of seedlings originally obtained by open pollination of parent clones.

Petunias are popular plants widely used as ornaments for bedding and potting during the summer growth season. There are numerous varieties which exhibit a wide range of properties. However, petunias normally have moderate growth rates, are annuals, grown from seed, have only moderate bloom concentration per plant, and are susceptible to heat. Accordingly, it is desired to obtain new varieties which will have rapid growth rates, be perennial, have substantial concentrations of blooms, and which will tolerate a wide range of temperatures and growing conditions.

DESCRIPTION OF THE FIGURES

FIG. 1 shows a typical plant in a hanging pot while FIGS. 2 and 3 show respectively a cluster of flowers and a closeup of specific flowers.

BOTANICAL DESCRIPTION OF THE VARIETY

Figure 1:
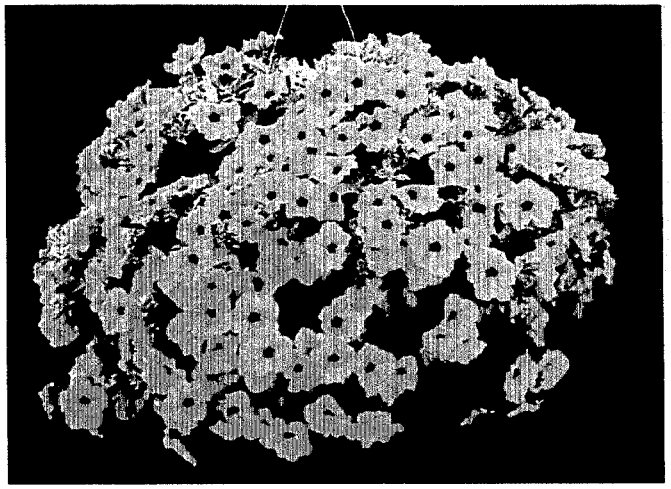
FIGS. 1, 2, and 3 are full color photographs of the new variety, taken at successively closer distances, showing the variety as grown in a nursery in Encinitas, Calif.
Figure 2:
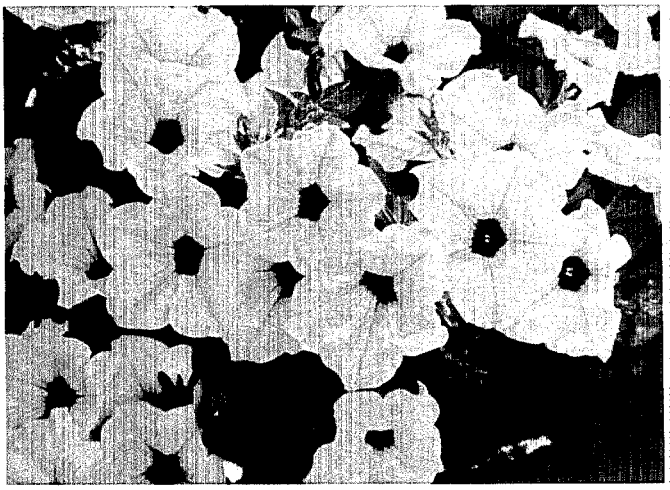
Figure 3:
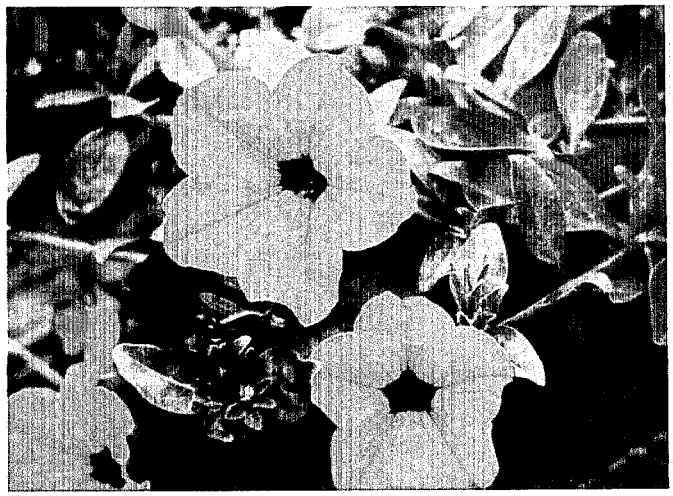

The claimed hybrid originated through open pollination of clones nos. 492X and 592Y, both respectively *petunia axillaris* hybrids, grown in close proximity to each other at Kientzler nursery, Gensingen, Baden-Wurttemburg, Germany, and transplanted to and selected at 60 Monbulk-Emerald Road, Emerald, Vistoria State, Australia. The integrity of the parent clone is preserved through asexual propagation by tip cuttings or aseptic culture. The resultant seedling progeny was grown to the flowering state and selections of clonal material were made on the basis of growth type, flower size and shape, color of foliage and flower, and spreading habit. Of the resulting plants the present "Pampas Fire" variety was selected as clearly meeting the intended goals of the propagation program.

Once the initial selections were made, another eight generations of cutting grown plants were subjected to extensive testing to insure homogeneity of the selections. Plants were tested and observed for susceptibility to fungal infestations, heat and cold endurance, performance on wet and drought conditions, flowering capability and speed of growth.

Plants vegetatively propagated and grown during the winter period in Victoria State, Australia, have proved tolerant to elevated summer ambient temperatures, up to about 113° F. (45° C.) and to chilly winter temperatures, down to slightly below 23° F. (–5° C.), for limited periods of time. The plant will not, however, survive prolonged periods of subfreezing winter temperatures or prolonged ground freezing. The optimum growing temperatures are in the range of 55°–65° F. (13°–18° C.), at which temperatures the typical growth time to mature plant is about 35 days at a daily level in the range of 7000–9000 foot candles (75,097 klx).

Samples of the claimed plants have also been subjected to salt spray conditions by plantings near the Pacific Ocean, in an area where extensive salt spray in the air is common. The test plants showed no visible damage over a four-month period, while plants of other genera subjected to the same conditions succumbed to the effects of the salt spray. The claimed plants may be considered to be suitable for planting in beachfront locations.

The plants are also resistant to high fertilizer concentrations which are toxic to many other types of plants. Plants will flower (in Victoria State, Australia) from early Spring through late Autumn provided that the soil pH does not exceed 6. At Encinitas, Calif., the plant first flowers in late March to Early April. At pH>6 iron deficiencies may occur which must be corrected with applications of chelated iron.

Colors described below are based on the Horticultural Colour Chart of The Royal Horticultural Society, London, England.

The plants described differ in significant aspects from the most closely related plants, which are the "Sweet Victory" Petunia plant selected and propagated by Applicant and the subject of a copending application for U.S. Plant Patent and the "Revolution Brillaintpink-Mini" petunia plant which is the subject of the U.S. Plant Pat. No. 6,914. A comparison table identifying these differences is et out below. All measurements stated are mean measurements.

TABLE

| Characteristic | "Pampas Fire"[1] | "Sweet Victory" | "Revolution Brilliantpink-Mini" |
|---|---|---|---|
| Stem length, cm | 83.4 | 83.4 | 76.1 |
| Stem pubescence | little | much | medium |
| Tube width, mm[2] | 15.4 | 16.6 | 16.8 |
| Leaf length, mm[3] | 66.2 | 56.5 | 73.1 |
| Leaf shape | ovate | ovate | broad elliptic |
| Leaf color | green | green | dark green |
| Corolla diameter, mm[4] | 71.1 | 58.4 | 66.2 |
| Pedicle length, mm | 28.4 | 14.1 | 26.9 |
| Pedicle diameter, mm | 1.63 | 1.42 | 1.62 |
| Petal color outside | RHS 80C | RHS 83D | RHS 80B–82B |

[1]The claimed plant
[2]Fully opened flower, at distel end of tube
[3]Largest leaves; a few early leaves are substantially larger
[4]Fully opened flower Species: *Petunia axillaris.*

Plant:

*Type.*—Perennial.

*Growth habit.*—Prostrate; diffuse spreading.

*Plant height.*—18 to 22 cm.

*Spreading area of plant.*—Approximately 1 m or more.

*Blooming period.*—Early September to late May in the state of Victoria, Australia; April to September in Encinitas, Calif.

*Root system.*—Fibrous.

Stem:

*Growth habit.*—Spreading, hanging.

*Texture.*—Viscid; hirsute.

*Thickness.*—Main stem, 6 mm, lateral stem, 3 mm.

*Branching.*—Abundant; diffuse

*Surface.*—Pubescence: Glandular.

Leaf:

*Phyllotaxis.*—Long persisting.

*Arrangement.*—At first whorled, later alternate.

*Internode distance.*—5–10 mm for vegetative shoot, 30–40 mm for flowering shoot.

*Texture.*—Somewhat fleshy.

*Shape.*—Entire; ovate; tip of blade obtuse; base attenuate.

*Size.*—Approximately 3–4 cm long×1–2 cm wide; early leaves commonly larger than later leaves; some early leaves are exceptionally large.

*Thickness.*—0.3 to 0.5 mm.

*Color.*—Yellow green (RHS 147A) above; yellow green (RHS 147B below.

Flower:

*Type.*—Axillary.

*Shape.*—Salverform; pendulous; having a hypogynous disk.

*Calyx.*—Five; parted petals united into a tube.

*Sepals.*—Oblanceolate; tips rounded, free to base; 25 mm long×5 wide.

*Corolla.*—4 cm long, limb to 8.5 cm.

*Color.*—Pink (RHS 66A), fading to lighter pink (RHS 66B) with age; backs of petals and tube violet (RHS 83C0; veins of petals and tube red purple (RHS 59A).

*Stamens.*—Five, four being didynamous, the fifth shortest; to 1.5 cm long; filaments pinkish purple (RHS 76B); anthers dark blue (RHS 45B).

*Pedicel.*—to 5 cm.

*Frangrance.*—typical of *P. axillaris.*

Fruit:

*Occurrence.*—Produced rarely.

*Type.*—Capsule with two undivided valves.

Seeds:

*Occurrence.*—Produced rarely.

*Shape.*—Spherical.

*Size.*—Minute.

I claim:

1. A new and distinct variety of *Petunia axillaris* plant named "Pampas Fire" as herein illustrated and described.

* * * * *